(12) United States Patent
Ashton et al.

(10) Patent No.: US 7,959,621 B2
(45) Date of Patent: Jun. 14, 2011

(54) ARRAY OF DISPOSABLE ABSORBENT ARTICLES HAVING A SEQUENCE OF GRAPHICS CORRESPONDING TO A WEARER'S STAGES OF DEVELOPMENT

(75) Inventors: Gregory Ashton, Cincinnati, OH (US); Molly Kelly Grovak, Chicago, IL (US); Kaoru Ishihara, West Chester, OH (US); Deborah Ann Vargo, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 365 days.

(21) Appl. No.: 12/146,711

(22) Filed: Jun. 26, 2008

(65) Prior Publication Data
US 2009/0030389 A1     Jan. 29, 2009

Related U.S. Application Data

(60) Provisional application No. 60/961,782, filed on Jul. 24, 2007.

(51) Int. Cl.
*A61F 13/15*      (2006.01)
*A61B 17/06*      (2006.01)
*B65D 85/00*      (2006.01)

(52) U.S. Cl. .............. 604/385.02; 604/385.01; 206/438; 206/459.5

(58) Field of Classification Search ............. 604/385.01, 604/385.02; 206/278, 524.1, 440, 438, 459.5
See application file for complete search history.

(56) References Cited

U.S. PATENT DOCUMENTS

| 2002/0072723 A1 | 6/2002 | Ronn et al. |
| 2003/0073966 A1 | 4/2003 | Sosalla |
| 2003/0114808 A1 | 6/2003 | Underhill et al. |
| 2003/0158532 A1 | 8/2003 | Magee et al. |
| 2007/0142798 A1 | 6/2007 | Goodlander et al. |

FOREIGN PATENT DOCUMENTS

| EP | 1 174 104 A | 1/2002 |
| JP | 2003-285890 A | 1/2002 |

OTHER PUBLICATIONS

International Search Report, mailed Jan. 22, 2009, PCT/IB2008/052856.

*Primary Examiner* — Jacqueline F. Stephens
(74) *Attorney, Agent, or Firm* — Laura L. Whitmer

(57) ABSTRACT

An array of disposable absorbent articles comprising a sequence of graphic designs corresponding to a wearer's stage of development. For a disposable diaper, the array of disposable absorbent article graphic designs may comprise a first absorbent article graphic design for newborns and infants, a second absorbent article graphic design for toddlers, and a third absorbent article graphic design for older wearers, and other absorbent article graphic designs.

17 Claims, 1 Drawing Sheet

ARRAY OF DISPOSABLE ABSORBENT ARTICLES HAVING A SEQUENCE OF GRAPHICS CORRESPONDING TO A WEARER'S STAGES OF DEVELOPMENT

CROSS REFERENCE TO RELATED APPLICATIONS

This application claims the benefit of U.S. Provisional Application No. 60/961,782, filed on Jul. 24, 2007.

FIELD OF THE INVENTION

The present invention is directed to an array of disposable absorbent articles having a sequence of graphics corresponding to a wearer's stages of development.

BACKGROUND OF THE INVENTION

Disposable absorbent articles such as diapers and catamenials are designed to absorb and contain bodily waste to prevent soiling of the body and clothing. The disposable absorbent articles typically comprise a single graphic design available in different sizes to fit a variety of wearers ranging from newborns to active toddlers. The design of the diaper typically affects performance, such as, ability to absorb and contain bodily waste. The size of the diaper typically affects fit, for example, the size of the diaper waist opening, the size of the openings around the thighs, and the length or "pitch" of the diaper.

The problem with having similar graphics across all sizes is that a single graphic design may not be appropriate for every age level of the wearer. Products that are white, or nearly white, may be appropriate for newborns and infants. Other graphic designs may also be desired as the toddler grows and becomes more interested in cartoon-like or entertaining graphics on the absorbent articles. As children get older, they may desire absorbent articles that do not look like traditional diapers, but rather, appear to be more underwear-like. This is especially true among wearers with a bedwetting problem. Bedwetting is an issue that millions of families face every night. It is extremely common among children who are under the age of 6, and it can last into the preteen years. Bedwetting can be very stressful for families. Children can feel embarrassed or guilty about wetting the bed and can be anxious about spending the night at a friend's house. Thus, there is a need for a variety of graphics for disposable absorbent articles matching a particular wearer's age level.

SUMMARY OF THE INVENTION

In accordance with the present invention, an array of disposable absorbent articles is provided comprising a sequence of graphic designs corresponding to a wearer's stages of development. For a disposable diaper, the array of disposable absorbent article graphic designs may comprise a first absorbent article graphic design for newborns and infants, a second absorbent article graphic design for toddlers, and a third absorbent article graphic design for older wearers, and other absorbent article graphic designs discussed further hereinafter in the detailed description of the invention.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

Figure 1:
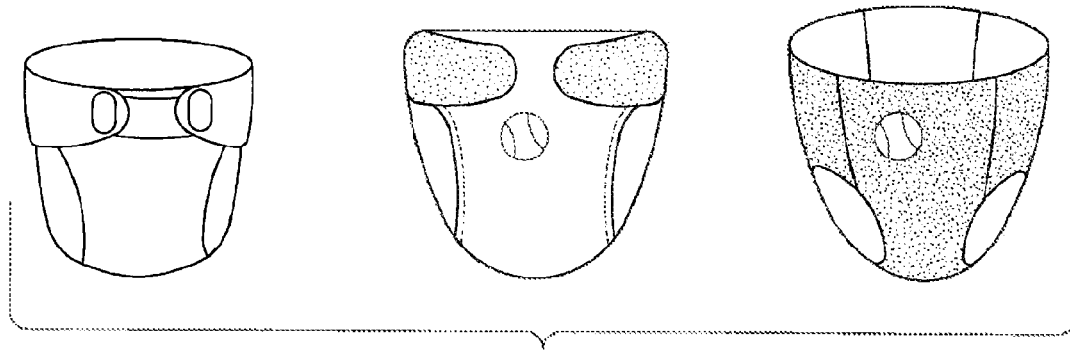
FIG. 1 is an array of absorbent articles in accordance with an embodiment of the present invention.

The present invention is directed to array of disposable absorbent articles having a sequence of graphics corresponding to a wearer's stages of development. For instance, the array of disposable absorbent article graphic designs may comprise a first absorbent article graphic design for newborns and infants, a second absorbent article graphic design for toddlers, and a third absorbent article graphic design for older wearers, and other absorbent article graphic designs.

As used herein, the term "absorbent article" refers to devices which are designed to absorb and contain bodily exudates, and, more specifically, refers to devices which are placed within, against, or in proximity to, the body of the wearer to absorb and contain the various exudates discharged from the body.

As used herein the term "chassis" refers to the main structure of the diaper with other features added to form the composite diaper structure.

As used herein the term "diaper" refers to an absorbent article generally used by infants and incontinent persons that is worn about the lower torso of the wearer.

The term "disposable" is used herein to describe absorbent articles which are generally not intended to be laundered or otherwise restored or reused as an absorbent article (in other words, they are generally intended to be discarded after a single use, and, preferably, to be disposed of in an environmentally compatible manner).

As used herein, the term "externally visible", as used in reference to an indicium associated with an article, refers to the ability of a human viewer to visually discern the indicium with the unaided eye (excepting standard corrective lenses adapted to compensate for near-sightedness, farsightedness, or astigmatism) in standard lighting conditions from a point of reference viewing the garment-facing surface of the article while the article is held in a configuration wherein the garment-facing surface is within the field of view.

As used herein, "graphic" is an identifying marking, which may include words and/or pictorials and/or designs and/or colors.

As used herein, "partially colored" means an absorbent article having at least about 25% of the surface area of the outer exposed portion of the chassis containing color that is externally visible under standard lighting conditions; alternatively, less than about 70% of the surface area of the outer exposed portion of the chassis containing color that is externally visible under standard lighting conditions.

References to identifying a "size" is used herein to include a direct or indirect identification of a disposable diaper or other absorbent article size, such as by number or letter (for example, "Size 3" or "Size A"), by direct description (for example, "Small" or "Large"), or by any combination thereof, and whether expressed or discernible visually, audibly or otherwise.

As used herein, the term "stage of development" refers to level of emotional and cognitive maturity and/or the physical abilities of an individual including locomotion, mobility, motor skills and coordination.

As used herein, "standard lighting conditions" refer to lighting conditions in which human vision operates efficiently (e.g., the human eye is able to discern complex patterns, shading, and colors). Specifically, for the purposes of describing this invention, standard lighting conditions are at least one of the following:

a) natural illumination as experienced outdoors during daylight hours, b) the illumination of a standard 100 watt incandescent white light bulb at a distance of 2 meters, or as defined by CIE D65 standard illuminate lighting at 800 lux to a 1964 CIE standard observer.

As used herein, "substantially colored" means an absorbent article having at least about 70% of the surface area of the outer exposed portion of the chassis containing color that is externally visible under standard lighting conditions, alternatively at least about 75%, alternatively at least about 80%, at least about 85%, at least about 90% of the surface area of the outer exposed portion of the chassis may contain color that is externally visible under standard lighting conditions.

As used herein, "substantially uncolored" means an absorbent article having less than about 25% of the surface area of the outer exposed portion of the chassis containing color that is externally visible under standard lighting conditions, alternatively less than about 20%, less than about 15%, less than about 10% of the surface area of the outer exposed portion of the chassis containing color that is externally visible under standard lighting conditions.

As used herein, "color" or "colored" or any variation thereof, does not include white.

Figure 2:
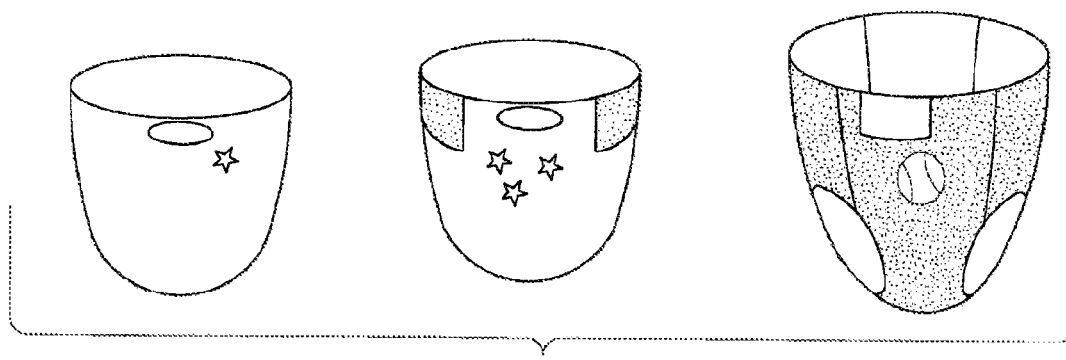
FIG. 2 is an array of absorbent articles in accordance with an embodiment of the present invention.
Figure 3:
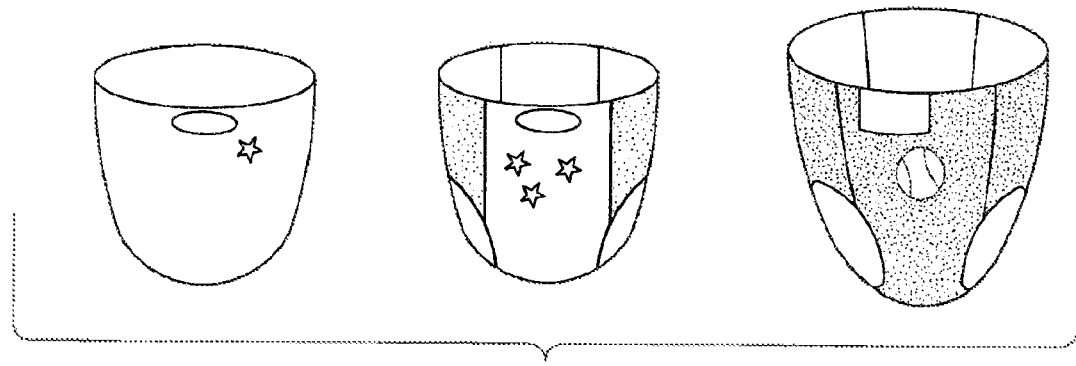
FIG. 3 is an array of absorbent articles in accordance with an embodiment of the present invention.

The array of absorbent articles described herein may be applicable to a number of absorbent article products. For instance, feminine hygiene garments may be made available in a variety of designs depending on a wearer's level of activity. However, a preferred embodiment includes an assortment of disposable diapers made available in a variety of product graphic designs where each design includes distinguishable characteristics addressing a wearer's stage of development. The stages of development may range from newborns to toddlers to older children having a bedwetting problem. For instance, a first stage of development might include newborns in a bonding stage with mom and other immobile infants whose absorbent article may be substantially uncolored, alternatively white. A second stage of development might include toddlers who are becoming interested in product graphics, shapes, characters, figures. The absorbent article may be partially colored. Alternatively, the absorbent article may display pastel colors; other versions of the second stage may display primary colors. Alternatively, the absorbent article may display gender specific graphics. A third stage of development might include older children who are having a bedwetting problem and want disposable absorbent articles to look more like underwear than diapers. This stage may desire absorbent articles that are substantially colored, thus appearing to look more like underwear. The absorbent articles of this stage may have gender specific graphics. Several potential embodiments of the array of absorbent articles are shown in FIGS. 1-3. Other stages of development and other embodiments are contemplated.

For each or any of the aforementioned stages of development, a separate absorbent article configuration may also be provided, in addition to the variety of graphic designs. For example, for the first stage of development, the absorbent article configuration may comprise a chassis designed to swaddle the wearer like a blanket and include a blanket like feel. This configuration might also include special structural features like an umbilical chord notch, wherein the absorbent article is substantially uncolored, alternatively white. White or substantially uncolored absorbent articles are preferred for the first stage of development, because some caregivers may perceive dyes/pigments to rub-off and transfer onto the skin. Thus, it may be desirable to have white or substantially uncolored absorbents articles for newborns or infants.

For the second stage of development, a second absorbent article configuration may comprise a chassis designed to gently conform to the wearer in order to enable more freedom of movement. For this second configuration, the chassis might be contoured having a relatively narrow crotch region, a stretchable high back region and a low cut front region and also include graphics, popular cartoon graphics, shapes, icons, etc. The absorbent article of the second configuration may be partially colored; some versions of this stage may display pastel color graphics, and other versions of this stage may display bright colors or primary colors. Alternatively, the absorbent article may be substantially colored. Alternatively, the absorbent article may display gender specific graphics. Alternatively, the second configuration may comprise a chassis having flexible fasteners and high stretch sides to facilitate easy, struggle-free changes of a toddler in a standing or lying position. Alternatively, the second absorbent article configuration may comprise a pull on chassis that a wearer can put on and off enabling him or her to participate in the dressing experience. The article may include a wetness indicator or training signal that enables the wearer to recognize the discomfort/ wet feeling associated with urination. Partially colored absorbent articles may be preferable for the second stage of development because children in this stage are beginning to learn and associate with images. Images only require partial color, as there needs to be white-space around the images to make them distinct from the background.

For the third stage of development, the configuration may comprise a pull on chassis that is designed to look more like underwear and having graphics such that the absorbent article is substantially colored. For this stage, the article configuration may comprise a chassis providing the comfort and look of underpants and the protection of a diaper, especially designed for older children with a bedwetting problem. For instance, the absorbent article may be designed to have a narrow crotch width and/or a thin, flexible core and/or stretch across most of the waist portion and/or gender specific graphics and/or all over color.

A bedwetting child who uses a disposable absorbent article is typically one who is toilet trained during the day, but still has accidents (urine only) at night, and is older than 4 or 5 years old. The child's incontinence may be a result of chemical imbalance, physiological development (e.g. delayed bladder development), psychological, or sociological issues. This incontinence issue presents a social restriction on the children who suffer from it, precluding the ability to participate in sleepovers or overnight camps without fear of overnight accidents.

The characteristics of a typical bedwetting child who uses a disposable absorbent article lead to key requirements of the disposable absorbent article. A bulky, large disposable absorbent article such as those that exist in the art might relieve containment concerns, but negate discretion, one of the key benefits of using an overnight product. Ideally, no one would know that the child was wearing a disposable absorbent article instead of underwear, providing the child with an underwear-like experience without the mess. Different product attributes that would help achieve discretion are the thickness of the product, the sound the product makes (diaper-like products are audible), age-appropriate graphics, characters, and colors, and shorter pitch. While it needs to achieve these means of discretion, it still needs to perform well in overnight containment situations, since a single accident can cause significant embarrassment for the child.

Since infants and toddlers experience stages of development at different rates, multiple sizes may be provided for each absorbent article graphic design. As a result, different absorbent article graphic designs are made available in overlapping size ranges. For instance, the first absorbent article graphic design might be available in a size one, a size two and a size three, while the second absorbent article graphic design might be available in a size three, a size four, a size five, and a size six. The third absorbent article graphic design might be available in a size a size six, a size seven, a size eight, and so on.

Overlapping size ranges related to design graphics make it difficult for a consumer to choose the right product configuration matching a particular wearer's stage of development. For this reason, a merchandising system is provided that facilitates consumers' selection of an absorbent article from a variety of design graphics and product configurations. The system preferably includes indicia exhibiting pictorial representations of the absorbent article design graphics and product configurations fitted to wearers' at corresponding stages of development. The indicia for the first absorbent article design graphics and product configuration might display an infant cradled in a mother's arms. Similarly, the indicia for the second absorbent article graphic design and product configuration might exhibit a toddler crawling or a mother changing the absorbent article while the wearer is standing or a wearer pulling the absorbent article up like underpants as the wearer participates in the dressing experience. Further, the indicia for the third absorbent article graphic design and product configuration might show older children running, smiling, and exhibiting confidence in themselves.

By matching the stage of development of a wearer with the stage of development exhibited by the indicia, the consumer can choose the right graphic design and product configuration for their particular wearer. The indicia may be provided on a display panel disposed above the store shelves on which the absorbent articles are displayed for sale. Alternately, the indicia may be disposed on packaging for the different absorbent articles or in advertisements disseminated to the public. The merchandising system may also include different product names associating each graphic design and product configuration with the particular stage of development for which the product is designed.

In addition to providing indicia displaying the absorbent article configurations in use and the different product names, the variety of absorbent article graphic designs and product configurations may be displayed on store shelves in an arrangement that facilitates the consumer's selection. For instance, the absorbent article configurations may be arranged in a first sequential order according to the stages of development and in a second sequential order according to size. For this arrangement, the first article displayed is the first absorbent article graphic design and product configuration, consecutively followed in the first direction by the second, third, and subsequent absorbent article graphic design and product configurations. The first, second, and third graphic design and product configurations are then arranged according to their available sizes in a second sequential order. For example, the first sequential order may be vertical with the first configuration displayed on a lowest shelf of the display and the third configuration displayed above on the highest shelf of the display, or vice versa. For this arrangement, sizes for each of the absorbent article configurations are arranged horizontally in the second sequential order with increasing sizes progressing from left to right. In an alternate embodiment, the sizes are arranged in columnar form to further facilitate the consumer's selection process. Optionally, the first sequential order may be horizontal across a given shelf with first, second, and third configurations displayed, progressing from left to right, on a given shelf. For this arrangement, the sizes for each absorbent article configuration are arranged vertically in the second sequential order with each shelf carrying a different size. In an alternate embodiment, the sizes are arranged such that each shelf in the display carries a different size in order to better distinguish the different product configurations; the sizes may progress upward or downward.

All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An array of disposable absorbent articles having a sequence of graphics corresponding to a wearer's stages of development, the array comprising:
   a first absorbent article, wherein the first absorbent article graphic design is substantially uncolored, such that less than about 20% of the surface area of the outer exposed portion of said absorbent article contains color;
   a second absorbent article, wherein the second absorbent article graphic design is partially colored, such that at least about 25% of the surface area of the outer exposed portion of said absorbent article contains color; and
   a third absorbent article, wherein the third absorbent article graphic design is substantially colored, such that at least about 80% of the surface area of the outer exposed portion of said absorbent article contains color, wherein said third absorbent article is designed for bedwetting children.

2. The array of disposable absorbent articles according to claim 1, wherein the wearers of said first absorbent article include newborn and infants.

3. The array of disposable absorbent articles according to claim 1, wherein the wearers of said second absorbent article include toddlers.

4. The array of disposable absorbent articles according to claim 1, wherein the wearers of said third absorbent article include older kids.

5. The array of disposable absorbent articles according to claim 1, wherein said first absorbent article is substantially uncolored, such that less than about 10% of the surface area of the outer exposed portion of said absorbent article contains color.

6. The array of disposable absorbent articles according to claim 1, wherein said second absorbent article is partially colored, such that less than about 70% of the surface area of the outer exposed portion of said absorbent article contains color.

7. The array of disposable absorbent articles according to claim 1, wherein said third absorbent article is substantially colored, such that at least about 90% of the surface area of the outer exposed portion of said absorbent article contains color.

8. The array of disposable absorbent articles according to claim 1, wherein said first absorbent article is white.

9. The array of disposable absorbent articles according to claim 1, wherein said second absorbent article contains cartoon or character graphics.

10. The array of disposable absorbent articles according to claim 1, wherein said second absorbent article include toddler relevant graphics.

11. The array of disposable absorbent articles according to claim 1, wherein said second absorbent article contains pastel colors.

12. The array of disposable absorbent articles according to claim 1, wherein said second absorbent article contains primary colors.

13. The array of disposable absorbent articles according to claim 1, wherein said third absorbent article contains gender specific graphics.

14. An array of disposable absorbent articles having a sequence of graphics corresponding to a wearer's stages of development, the array comprising:
  a first absorbent article, wherein said first absorbent article is substantially uncolored, such that less than about 20% of the surface area of the outer exposed portion of said absorbent article contains color;
  a second absorbent article, wherein said second absorbent article is partially colored and comprises pastel colors, such that at least about 25% of the surface area of the outer exposed portion of said absorbent article contains color; and
  a third absorbent article, wherein said third absorbent article is substantially colored, such that at least about 80% of the surface area of the outer exposed portion of said absorbent article contains color, and comprises gender specific graphics.

15. The array of disposable absorbent articles according to claim 14, wherein said third absorbent article is designed for bedwetting children.

16. An array of disposable absorbent articles having a sequence of graphics corresponding to a wearer's stages of development, the array comprising:
  a first absorbent article, wherein said first absorbent article is substantially uncolored, such that less than about 20% of the surface area of the outer exposed portion of said absorbent article contains color, wherein said first absorbent article corresponds to a first stage of development;
  a second absorbent article, wherein said second absorbent article is partially colored, such that at least about 25% of the surface area of the outer exposed portion of said absorbent article contains color, wherein said second absorbent corresponds to a second stage of development that occurs after said first stage of development; and
  a third absorbent article, wherein said third absorbent article is substantially colored, such that at least about 80% of the surface area of the outer exposed portion of said absorbent article contains color, wherein said third absorbent article corresponds to a third stage of development that occurs after said second stage of development.

17. The array of disposable absorbent articles according to claim 16, wherein said third absorbent article is designed for bedwetting children.

* * * * *